United States Patent [19]
Timmons, II et al.

[11] Patent Number: 5,620,097
[45] Date of Patent: Apr. 15, 1997

[54] PROTECTIVE PACKAGING SYSTEM

[75] Inventors: Dicky D. Timmons, II, Somerville, N.J.; E. Hubbard Yonkers, Contoocook, N.H.

[73] Assignee: Ortho Pharmaceutical Corporation, Raritan, N.J.

[21] Appl. No.: 367,043

[22] Filed: Dec. 30, 1994

[51] Int. Cl.⁶ ..................... B65D 81/02
[52] U.S. Cl. ..................... 206/521; 206/456
[58] Field of Search ..................... 206/456, 454, 206/521, 583, 526, 814, 460

[56] References Cited

U.S. PATENT DOCUMENTS

| | | | |
|---|---|---|---|
| 2,165,539 | 7/1939 | Dahlgren | 206/460 |
| 3,489,265 | 1/1970 | Puente | 206/454 |
| 4,589,551 | 5/1986 | Hellon | 206/456 |
| 4,763,789 | 8/1988 | Questal et al. | 206/454 |
| 5,044,500 | 9/1991 | Webber et al. | 206/456 |
| 5,090,568 | 2/1992 | Tse | 206/456 |
| 5,147,042 | 9/1992 | Levy | 206/454 |
| 5,353,934 | 10/1994 | Yamauchi | 206/454 |

FOREIGN PATENT DOCUMENTS

| 3239460 | 4/1984 | Germany | 206/521 |
|---|---|---|---|

*Primary Examiner*—David T. Fidei
*Attorney, Agent, or Firm*—Paul A. Coletti

[57] ABSTRACT

A protective packaging system that will house a fragile object during transport or mailing without using bulky packaging materials. The package is essentially flat and conforms in overall dimensions to a standard mailing envelope while providing heightened protection for the object contained therein. The protective packaging system includes an envelope and a receptacle received within the envelope for the transport of generally thin, flat, flexible, yet fragile goods. In accordance with a presently preferred embodiment, the protective packaging system is designed to safely transport medical test specimens such as dried blood spots (DBSs) or other dried bodily fluids borne by a test card constructed as a flexible substrate. The envelope and receptacle combination are flexible enough to pass through the automated equipment of the United States Postal Service (or other carrier service) yet rigid enough to withstand the handling encountered in the mails so as to avoid damage to the package's contents. The receptacle includes structure for facilitating insertion of an object into the receptacle as well as structure for covering and protecting predetermined areas of the object.

79 Claims, 9 Drawing Sheets

PROTECTIVE PACKAGING SYSTEM

FIELD OF THE INVENTION

The present invention relates generally to packages and, more particularly, to a protective packaging system for shipping fragile objects.

BACKGROUND OF THE INVENTION

A broad assortment of insulation and packaging materials are presently used to transport payloads which are prone to crushing, tearing or other breakage. Included among these are a multitude of containers fashioned from exotic composite materials and from such mundane materials as cardboard for safely transporting payloads which are unstable of fragile.

Additionally, the prior art discloses various padding or filler materials that are useful as impact insulation within a box, envelope or other shipping container. For instance, materials such as corrugated cardboard, used alone or in conjunction with plastic "bubble wrap," foam beads, foam "peanuts" or the like, generally represent state-of-the-art in protecting fragile objects during shipping. In the absence of such packing materials, however, conventional unpadded shipping containers are either too flimsy to reliably protect highly fragile contents if delivered through the mail or too rigid to be processed by automated postal service machinery. In the latter case, the containers must be hand-processed by the postal carrier, thereby delaying their delivery.

Despite the general efficacy of most packaging materials as protectants, the result has often been an ungainly package which is typically substantially larger and, frequently, many times greater in size than the goods contained therewithin. In fact, in order to insure the requisite degree of protection, a relatively small and fragile object normally must be surrounded by considerable amounts of packing materials. Consequently, similar to packages that are too rigid for automated processing, the United States Postal Service or other carrier commonly must process such bulky packages by hand.

This problem is especially frustrating with respect to relatively flat, fragile goods which otherwise fit readily within the spacial confines of conventional envelopes or mailers suitable for automated postal processing, yet, because of their delicate nature, cannot endure the rigors of automated postal facility processing machinery or the stresses associated with manual handling. Under these circumstances, polymeric materials would seem an attractive means by which to encase such goods for transport. However, notwithstanding their inherent elastic memory qualities, most packages formed from polymeric materials are subject to cracking or deformation when subjected to conventional processing and handling techniques. Consequently, there is no presently available package design that incorporates light weight, high strength and small size with resistance to repeated bending and handling procedures.

An advantage exists, therefore, for a lightweight, protective shipping package that is flexible enough to pass through the automated equipment of the United States Postal Service (or other carriers), yet is sufficiently rigid to withstand the jostling and other rough handling typically encountered in the mails.

SUMMARY OF THE INVENTION

The present invention provides a package that will protectively house a fragile object during transport or mailing without using bulky packaging materials. The package is essentially flat and conforms in overall dimensions to a standard mailing envelope while providing heightened protection for the object contained therein.

More particularly, the instant protective packaging system comprises an envelope and receptacle for the transport of generally thin, flat, flexible, yet fragile goods. As such, it is contemplated that the packaging system of the present invention may be readily adapted to accommodate sundry delicate objects including, but not limited to, documents, photographs, and floppy computer disks. In accordance with a presently preferred embodiment, the protective packaging system is designed to safely transport medical test specimens such as dried blood spots (DBSs) or other dried bodily fluids borne by a test card constructed as a flexible substrate. The envelope and receptacle combination are flexible enough to pass through the automated equipment of the United States Postal Service (or other carrier service), yet rigid enough to withstand the handling encountered in the mails so as to avoid damage to the package's contents. The envelope may be made of any suitable flexible yet rugged material and, preferably, is fabricated from paper or plastic, e.g., spun polyolefin such as Tyvek®. When paper is used, a suitable material may be solid, bleached, sulfite stock ("SBS" stock).

Likewise, the receptacle may be made from any material of suitable flexibility and durability such as, for example, plastic, cardboard, chip board, metal, composite products, or any combination thereof.

Preferably, however, the receptacle is fabricated from polymer plastic for example, polyethylene terephthalate, polyvinylchloride, polycarbonate, polyacrylate or polyurethane. At present, the preferred material is polyethylene terephthalate glycol ("PETG"). The receptacle may be formed by a thermoforming process. Essentially, thermoforming of the receptacle entails running a thin (approximately 13 to 16 mils) polymer web or sheet through a heated male and female form whereby numerous structurally and functionally designated raised and indented surfaces are formed in the receptacle. After forming, the thermoformed receptacle may then be die cut (rotary or otherwise) to assume the shape of a foldable member having first and second panels adapted to be folded upon and secured to one another to establish an object receiving pocket.

Among other features, the receptacle preferably includes various means which facilitate insertion of a medical specimen test card or other flexible, substantially flat, fragile object into the receptacle. It is contemplated that these means may include opposing ramps which spread the receptacle and envelope surfaces as the object is inserted and close behind and retain the object once it is fully inserted into the receptacle. If the object is a medical specimen test card, for example, the ramps also reduce the likelihood of damaging, during insertion, bodily fluid spots (e.g., blood spots) that may be borne by the card. Other means such as one or more sets of opposed guides may be provided to assist in directing the object into a proper position and/or maintaining such position during insertion.

According to a presently preferred embodiment wherein the receptacle functions to receive and protect a medical specimen test card therein, the receptacle further comprises one or more raised, substantially dome-shaped protective areas or chambers which are preferably formed in both the first and second panels of the receptacle. When the receptacle is folded and its first and second panels are secured to one another these raised protective areas or domes desirably reside along opposite end edges of the receptacle. The purpose of the domes is to cover and protect the dried bodily fluid spots on the test card during transport without coming into contact with same. Further, by being raised, the domes also allow for airflow to assist in the drying of the spots in the event that they are still wet when they are inserted into the receptacle. The domes are preferably generally oval or circular shape in plan view. The circumferential walls of the domes may be continuous or discontinuous. If discontinuous, as preferred, these discontinuities or gaps also permit airflow as well as reduce the possibility that the receptacle will come into contact with the bodily fluid spots during card insertion and package transport.

Since the opposed sets of domes desirably appear in both the first and second receptacle panels and at the leading and trailing end edges of the receptacle when folded, the domes may accommodate the test card regardless of whether the card is inserted with bodily fluid spots at the leading or trailing edge of the card or whether the spots face the first or second receptacle panel. It should be noted that if blood is borne by the test card, the blood may be inserted into the envelope when wet. However, the National College of Clinical Sciences (NCCS) requires that the blood spots not be exposed to possible human contact, i.e., that the spots be covered on both sides during transport, which coverage is provided by the domes of the preferred receptacle. As mentioned, optional gaps may be provided in the circumferential areas of the domes. If provided along the domes' longitudinal axes (i.e., axes which essentially parallel the longitudinal axis of the receptacle), these gaps act as vents to promote vapor transmission related to the drying of the bodily fluid spots. Additional gaps may be provided generally along the domes' transverse axes to enhance flexibility of the receptacle member as well as bodily fluid drying. If a plurality of domes are arranged in an array, the overall shape of the array and the dimensions of the individual domes are sufficiently large to allow limited tolerance for a card which may become slightly mispositioned during shipment.

When the receptacle is folded, one of the first and second receptacle panels preferably defines a pair of longitudinally projecting leg members. The legs of the receptacle give the overall structure of the mailer a favorable balance of rigidity and flexibility as well as prevent the receptacle from moving about inside the envelope during shipment.

The receptacle may also include apertures which may appear at any of several locations throughout the receptacle. For example, some apertures may be provided along the fold line between the first and second receptacle panels. Such apertures would operate to reduce the elastic memory of the plastic, lighten the weight of the mailer and provide additional venting to precipitate drying of the bodily fluid spots. Similarly, one or both of the receptacle panels may have one or more other holes of suitable size, shape, and location to facilitate drying of the bodily fluid spots as well as to reduce the weight and elastic memory of the plastic.

It should also be noted that when blood is dried it is not considered infectious. But, if dried blood is rehydrated, then it is considered to be potentially infectious. However, even if dried blood spots on a medical specimen test card that was properly inserted into the protective packaging system of the present invention were subsequently rehydrated, the test card would be effectively retained within the receptacle, which in turn is surrounded by the envelope, thereby rendering the probability of human contact with the blood spots virtually nil, even if the envelope seal flap has not yet been closed.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
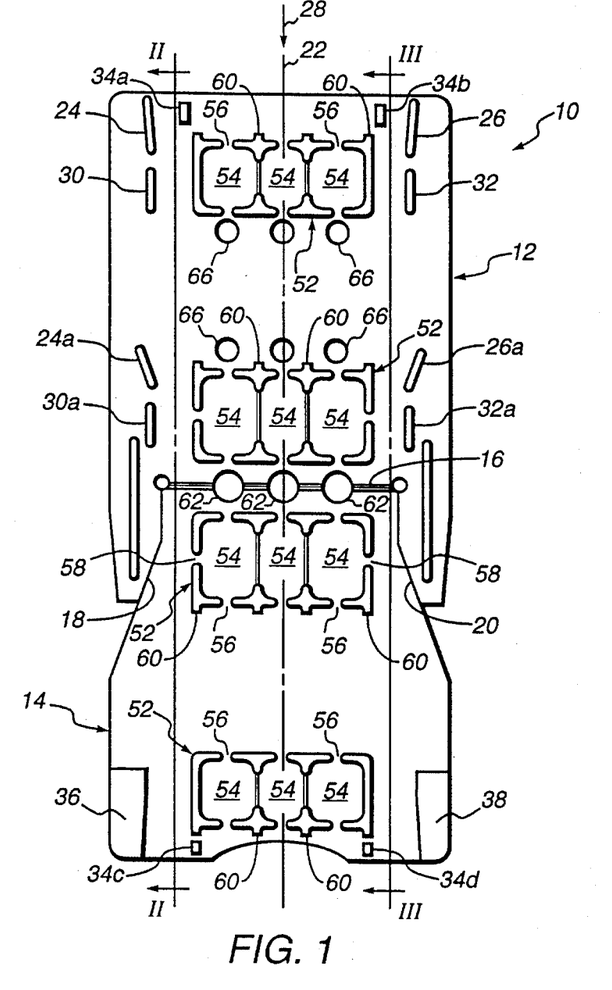
FIG. 1 is a top plan view of a preferred embodiment of an unfolded receptacle member of the protective packaging system of the present invention.

Referring to the drawings wherein like reference characters designate like or corresponding parts throughout the several views, there is shown a top plan view of a presently preferred embodiment of an receptacle member 10 of the protective packaging system of the present invention. The receptacle member may be made from any material of suitable flexibility and durability to enable the receptacle member, and thus the entire protective packaging system, to be flexible enough to pass through the automated processing equipment of the United States Postal Service (or the carrier service) yet rigid enough to withstand the handling encountered in the mails so as to avoid damage to the package's contents. Examples of materials from which receptacle member 10 may be formed include, without limitation, plastic, cardboard, chipboard, metal, composite products, or any combination thereof.

Preferably, however, the receptacle member is fabricated from polymer plastic for example, polyethylene terephthalate, polyvinylchloride, polycarbonate, polyacrylate or polyurethane. Regardless of the composition of the chosen receptacle material, such material should be flexible, resistant to extremes in temperature and cracking, and have sufficient elastic memory to restore itself to a substantially flat conformation after repeated bending. At present, the preferred receptacle material is polyethylene terephthalate glycol ("PETG"). If made from polymeric material, the receptacle member 10 may be formed by a thermoforming process. Essentially, thermoforming entails running a thin (approximately 13 to 16 mils) polymer web or sheet through a heated male and female form. Numerous structurally and functionally designated protrusions, which will be described in detail hereinafter, may be formed in the receptacle during the thermoforming process. After forming, the thermoformed receptacle member 10 may then be die cut (rotary or otherwise) to assume the shape of a foldable member having first and second panels 12, 14 connected by a common hinge means 16. The first and second panels 12 and 14 are adapted to be folded upon and secured to one another in spaced apart, substantially facing relation to establish an object receiving pocket therebetween. To facilitate folding of the receptacle member 10, the first and second panels are severed from one another by cuts 18 and 20 which terminate at hinge means 16.

The following discussion of the first and second receptacle panels 12, 14 refers to various means and structure which may be provided to either the first or the second panel. In this regard, the designations of means or structure associated with the first panel 12 and second panel 14 are merely to facilitate understanding of the present invention with reference to the drawing figures. It will be understood, therefore, that any and all means or structure herein described as being associated with the first panel 12 may just as well be formed in or otherwise provided to the second panel 14, and vice versa. Further, although illustrated as being hingedly joined at common end edges, the panels 12, 14 may be joined at common side edges. In the alternative, panels 12, 14 may be formed separately and subsequently secured in spaced apart, substantially facing relation.

The first and/or second panels 12, 14 are provided with at least one or, more preferably, several means which individually and collectively serve to facilitate proper insertion of an object into the receptacle member when such is arranged to form an object receiving pocket (described in greater detail hereinafter) such as in the manner shown in FIG. 4. To that end, the first panel 12 preferably includes first guidance means for displacing a substantially flat object (an example of which is discussed below) into a position substantially parallel to and symmetrical with a generally centrally located insertion axis 22 of the receptacle member 10 when the object is inserted into the receptacle. The first guidance means desirably comprises at least one pair of opposed guide members 24 and 26 formed in and projecting upwardly from the first panel 12. The guide members 24, 26 are located along opposite side edges of the first panel and are angled inwardly toward the insertion axis 22 in the direction of insertion of the object as indicated by arrow 28. If contacted by an object being inserted into the object receiving pocket, guide members 24, 26 effect laterally inward displacement of the object as it is being inserted into the receptacle member. For optimum performance, the first guidance means preferably additionally includes at least one additional pair of similarly constructed angled guide members 24a and 26a. With arrow 28 as a point of reference, guide members 24a, 26a are located downstream from guide members 24, 26.

Although not illustrated, one or both of the panels 12, 14 may be provided with reinforcement means such as one or more ribs or similar structure extending between and substantially transversely to the panels' side edges. Such reinforcement means would permit bending of the receptacle member, when folded, in the direction of the insertion axis 22, as it is that direction in which the receptacle member would bend when passing through automated postal service processing machinery. By contrast, the reinforcement means would cause the folded receptacle member to resist bending in a direction transverse to the insertion axis.

The first panel 12 also preferably carries second guidance means for assisting the object in maintaining its substantially parallel orientation via-a-vis the insertion axis 22 as it passes the aforementioned first guidance means. The second guidance means preferably includes at least one pair of opposed guide members 30 and 32 formed in and projecting upwardly from the first panel 12. The guide members 30, 32 extend substantially parallel to the insertion axis 22 and are situated downstream of the angled guide members 24 and 26, respectively, of the first guidance means. Guide members 30 and 32 and the downstream ends of the angled guide members 24 and 26 are preferably spaced from the side edges of the first panel by substantially equal distances. The second guidance means may also include at least one additional pair of guide members 30a and 32a which respectively extend substantially colinearly with guide members 30 and 32. Further, if the first guidance means includes angled guide members 24a and 26a, the additional pair of second guidance means guide members 30a, 32a should be positioned relative to angled guide members 24a, 26a in a manner similar to that in which second guidance means guide members 30 and 32 are disposed relative to angled guide members 24, 26. As the reader will appreciate, the presence of second guidance means guide members 30a, 32a assures that the object maintains proper alignment at its leading end as the trailing end of the object enters the receptacle. Additionally, although they permit some limited lateral movement of the object, the first and second guide means prevent the object from shifting within the receptacle member to any degree that would cause harm to the object during transport of the package.

Figure 3:
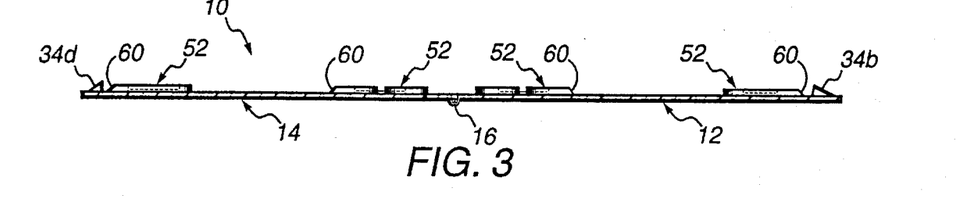
FIG. 3 is an elevational cross-section view of the receptacle member of FIG. 1 taken along line III—III thereof.

Receptacle member 10 additionally preferably includes stabilizing means carried by at least one of the first panel 12 and the second panel 14 for urging the object to enter the receptacle member along a plane extending substantially parallel to the plane of first panel during insertion of the object into the object receiving pocket. The stabilizing means may comprise at least one or, more preferably, a pair of spaced apart ramp members formed in and projecting upwardly from at least one of the first and second panels 12, 14 adjacent the opposite end edges thereof, i.e., adjacent the end edges distant from the hinge means 16. As is most clearly shown in FIGS. 3, 5 and 7A, these ramp members, designated herein by reference numerals 34a, 34b, 34c and 34d, slope outwardly from the surface(s) of the first and/or second panels 12, 14 toward hinge means 16. Most preferably, the ramp members 34a–34d comprise two cooperating pairs of ramp members with ramp members 34c and 34d of second panel 14 being so disposed to nest between ramp members 34a and 34b of first panel 12 as depicted in FIGS. 4, 6 and 8B. It is also contemplated that ramp members 34a and 34b may alternatively be arranged to nest between ramp members 34c and 34d. The function of the ramp-type stabilizing means will be more fully appreciated by reference to the description of FIGS. 6 through 8B, infra.

Figure 4:
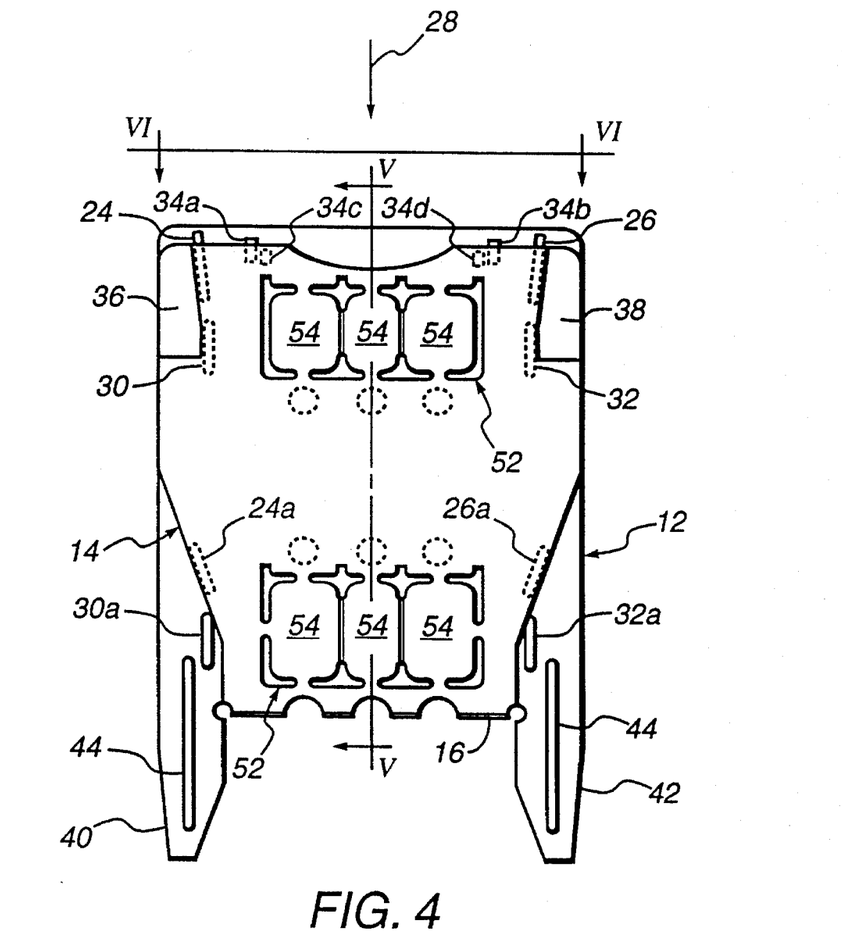
FIG. 4 is a plan view of the receptacle member of FIG. 1 in folded condition.

To secure the first and second panels 12, 14 into the folded condition shown in FIG. 4, the second panel 14 is desirably provided with a pair of opposed protruding notches 36 and 38 positioned along its respective side edges which may be spot-welded or adhesively attached to the surface of the first panel 14. Alternatively, other suitable means such as snap-type fasteners may be formed in or attached to the first and second panels to permanently or releasably connect the panels to one another in spaced apart, substantially facing relation. The cuts 18, 20 separating the first panel from the second panel establish, when the second panel is folded over onto the first, a pair of legs 40 and 42 projecting from the first panel in a direction away from hinge means 16. To rigidify the legs 40, 42 and thus the folded receptacle member 10, each of the legs are also preferably provided with at least one elongated stiffening rib 44. The function of the legs 40, 42 will be more fully understood by reference to the description of FIGS. 10–12, infra.

Figure 9:
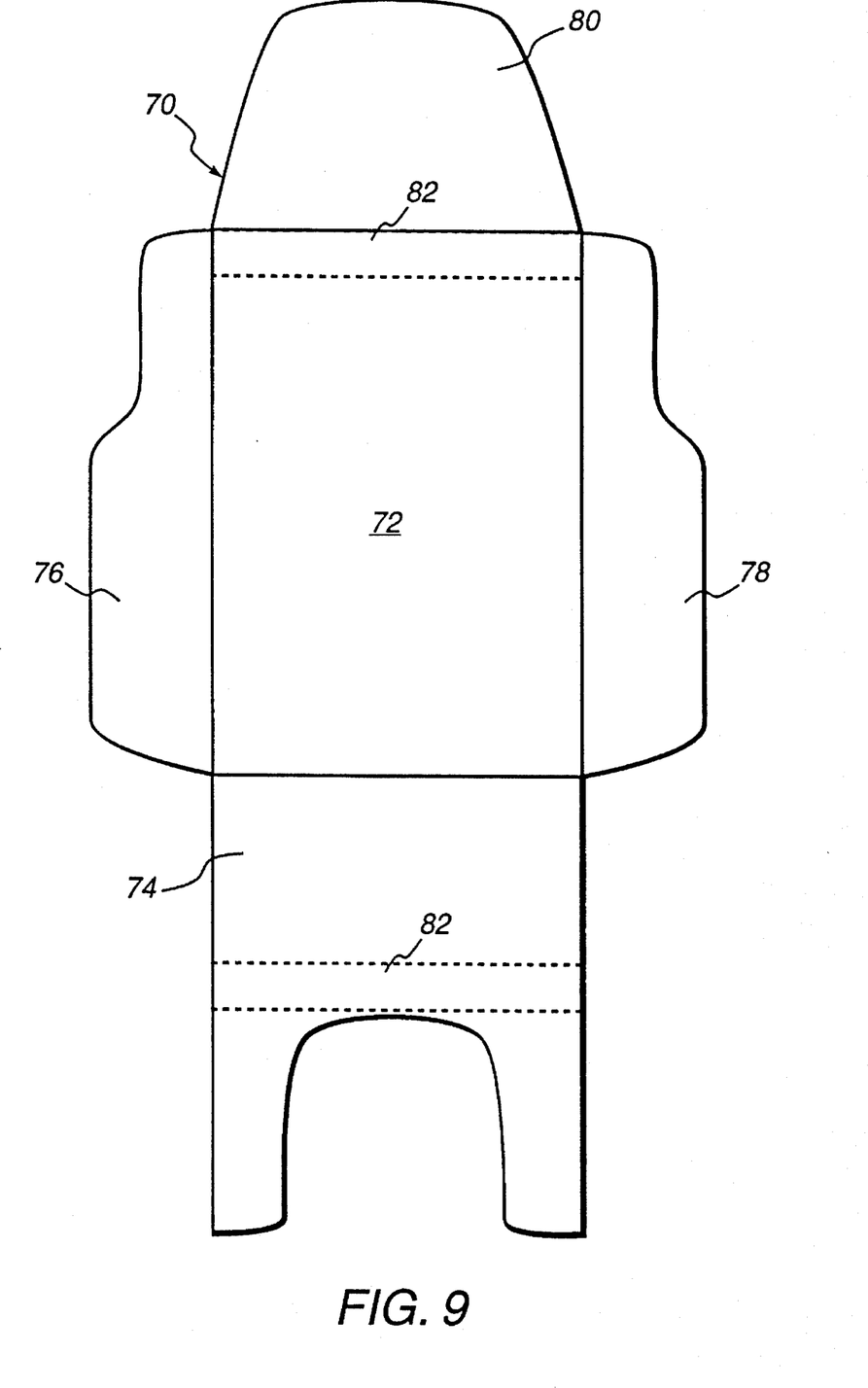
FIG. 9 is a top plan view of a preferred embodiment of an envelope of the protective packaging system of the present invention.

Possessing no more structure than that thus far discussed, the receptacle member 10, when constructed as described and received within a mailing envelope such as that shown in FIG. 9, can be effectively deployed as a protective package for safely transporting substantially flat, delicate objects such as documents, photographs and floppy computer disks, among others. The package would be sufficiently flexible to be rapidly processed by automated postal service machinery and sufficiently rigid to withstand the attendant rigors of shipping and handling.

Figure 7:
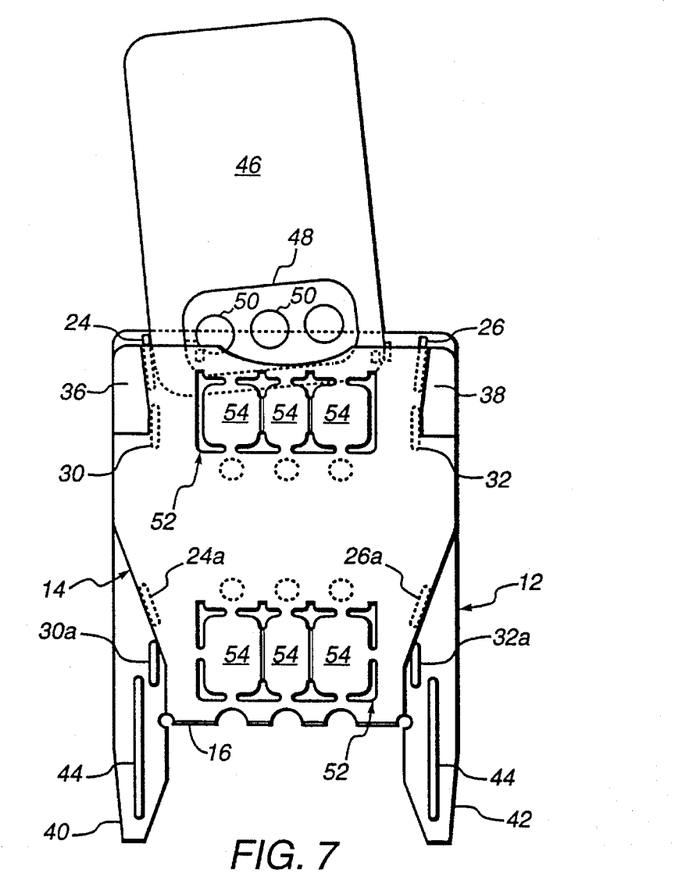
FIG. 7 is a plan view similar to FIG. 4 with an object shown partially inserted into the folded receptacle member.
Figure 8:
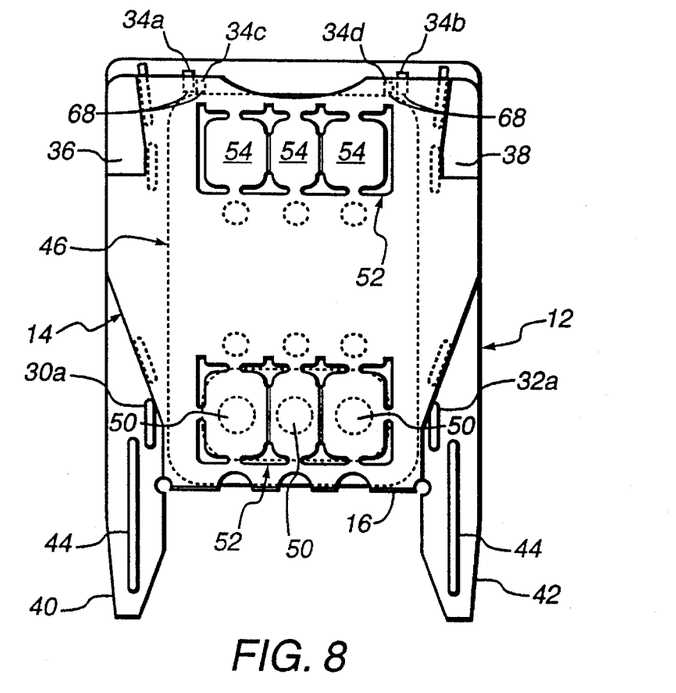
FIG. 8 is a plan view similar to FIG. 7 with an object shown fully inserted into the folded receptacle member.

In accordance with a presently preferred embodiment, the receptacle member 10 is particularly well suited to safely transport medical test specimens such as dried blood spots (DBSs) or other dried bodily fluids borne by a test card constructed as a flexible substrate. FIGS. 7 and 8 perhaps most clearly show the general construction of a medical specimen test card, identified by reference numeral 46, adapted for insertion into receptacle member 10 of the present invention. The test card 46 is substantially flat, somewhat flexible, and generally rectangular in shape. It may be formed of any suitable material such as cardboard or plastic and comprises a test window 48 that exposes filter paper or other collection medium onto which one or more samples of bodily fluids 50, e.g., blood spots, may be blotted.

In this connection, referring again to FIGS. 1 and 4, either or both of the first and second panels 12, 14 of receptacle member 10 may be further provided with structure defining means specifically adapted for covering and protecting at least one predetermined area of an object to be inserted into the receptacle member, e.g., the medical test specimens carried by the test card 46. This structure, designated by reference 52, preferably comprises at least one formation protruding upwardly from the surface of each of panels 12, 14 of a size sufficient to encompass the area of at least one bodily fluid sample 50. Structure 52 may be provided in the panels adjacent the hinge means 16, adjacent the opposite end edges of the panels or, more preferably (as illustrated), at both of these sites. Moreover, depending upon the location and number of the test window(s) 48 in test card 46, structure 52 may be situated at any position on panels 12, 14 between their opposite end edges and the hinge means. Preferably, the configuration and location of structure 52 is substantially identical on both of panels 12, 14 such that when the second panel 14 is disposed in facing relation to the first panel 12 as shown in FIG. 4, structure 52 of panel 14 substantially aligns with structure 52 of panel 12. Additionally, the height to which structure 52 protrudes from the surface of panels 12, 14 is preferably approximately one-half the height of guide members 24, 26, 30, 32, etc., such that, when folded, the insert member assumes a generally flat conformation.

As previously mentioned, structure 52 may be configured as a single chamber-like formation adapted to encompass a single bodily fluid sample 50. Alternatively, it may, as shown, comprise a plurality of chambers arranged in an array corresponding to the locations of the bodily fluid samples 50 in the test card window 48. Whether structure 52 is constructed as a single chamber or as a plurality of chambers arranged in an array, the overall shape of the array and the circumferential dimensions of the individual chambers are sufficiently large to allow limited tolerance for a test card which may become slightly mispositioned during shipment.

Figure 5:
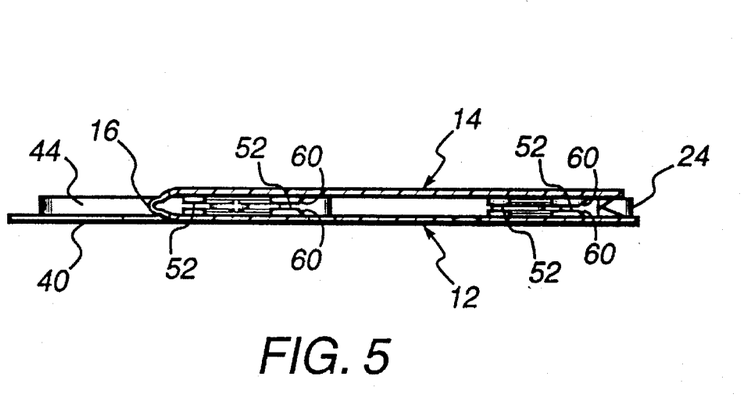
FIG. 5 is an elevational cross-section view of the folded receptacle member of FIG. 4 taken along line V—V thereof.
Figure 6:
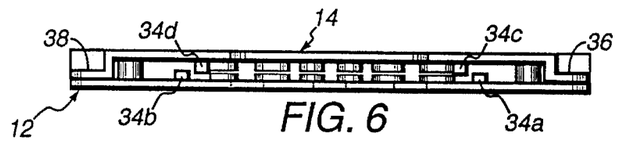
FIG. 6 is an enlarged end view of the folded receptacle member of FIG. 4 as seen from line VI—VI thereof.
Figure 7A:
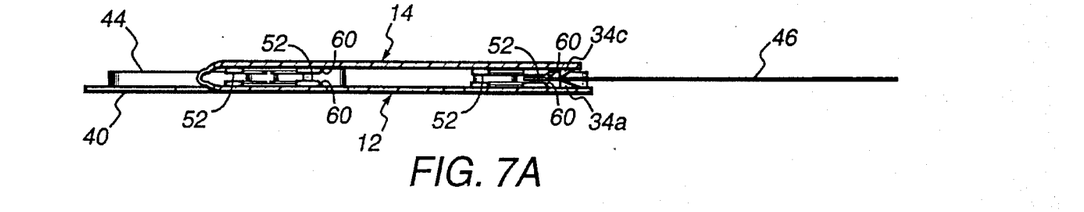
FIG. 7A is an elevational cross-section view similar to FIG. 5 with an object inserted into the folded receptacle member to the extent shown in FIG. 7.
Figure 8A:
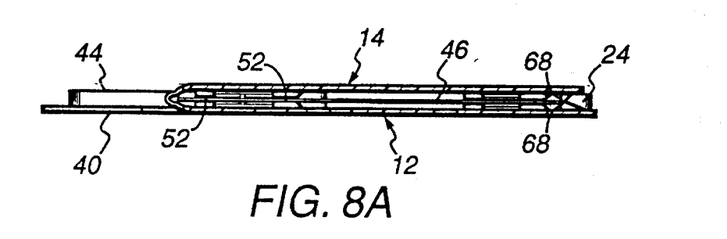
FIG. 8A is an elevational cross-section view similar to FIG. 7A with an object shown fully inserted into the folded receptacle member.
Figure 8B:
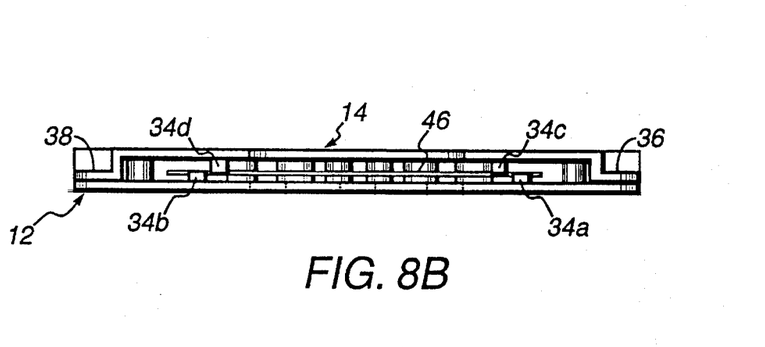
FIG. 8B is an enlarged end view of the folded receptacle member similar to FIG. 6 with the object fully inserted therein.

As best appreciated by reference to FIGS. 5, 7A and 8A, the chamber-like means defined by structure 52 for covering and protecting the medical test specimens carried by the test card 46 comprise raised dome-shaped protective areas or, simply, domes 54 established by the respective surfaces of panels 12, 14 which are bounded by the interior peripheral walls of structure 52. The domes 54 cover and protect the dried bodily fluid spots 50 on the test card 46 during transport without coming into contact with same. Further, by being raised, the domes also allow for air flow to assist in the drying of the spots in the event that they are still wet when they are inserted into the receptacle member 10. The domes are preferably generally oval or circular shape in plan view, although they may assume any shape sufficient to encompass the bodily fluid spots on the test card.

As stated above, it is preferred that corresponding structure 52 be provided in each of the insert panels 12, 14 adjacent both sides of the hinge means 16 and along the opposite end edges of the panels. So constructed, opposed sets of domes 54 would appear in both the first and second receptacle panels at the hinged downstream (or "leading") edge and the upstream (or "trailing") edge of the receptacle member 10 when folded. Consequently, the domes 54 accommodate the test card 46 regardless of whether the card is inserted with bodily fluid spots 50 at the leading or trailing edge of the card or whether the spots face the first or second insert panel. It should be noted that if blood is borne by the test card, the blood may be inserted into the package when wet. However, the National College of Clinical Sciences (NCCS) requires that blood spots not be exposed to possible human contact, i.e., that the spots be covered on both sides during transport, which coverage is provided by the domes 54 of receptacle member 10.

The circumferential shape of structure 52 defining the walls of the domes 54 may be continuous or, preferably, discontinuous, i.e., the walls of the domes may be provided with one or more gaps. If provided along the domes' longitudinal axes (i.e., axes which essentially parallel the insertion axis 22) these gaps (reference numeral 56) act as vents to promote vapor transmission related to the drying of the blood spots. Additional gaps 58 may be provided generally along the domes' transverse axes to enhance flexibility of the receptacle member 10 as well as bodily fluid drying. In either event, the gaps 56 and/or 58 also reduce the likelihood that the receptacle member will come into contact with the bodily fluid spot(s), during card insertion and package transport.

Structure(s) 52 further desirably include means for facilitating movement of the test card 46 once it is inserted into the receptacle member. As perhaps most clearly shown in FIGS. 3, 5 and 7A, this means preferably comprises at least one ramp member 60 integral with structure(s) 52. Ramp member(s) 60 slope outwardly from the surface of at least one of the panels 12, 14 toward hinge means 16 such that, when the receptacle member 10 is folded as in FIG. 4, the ramp member(s) 60 are presented upstream of the respective structure(s) 52. Ramp member(s) 60 assure that the test card 46 slides smoothly past the structures as it is inserted into the receptacle member. Without the ramp member(s) 60 the test card might otherwise collide with the walls of structure(s) 52 and possibly become damaged upon insertion.

The receptacle member 10 may also include apertures which may appear at any of several locations throughout the receptacle member. For example, some apertures 62 may be provided along the hinge means 16. Such apertures would operate to reduce the elastic memory of the plastic, lighten the weight of the mailer and provide additional venting to precipitate drying of bodily fluid spots. Similarly, one or both of the receptacle panels may have one or more holes, such as holes 66, of suitable size, shape and location to enhance drying of the bodily fluid spots as well as to reduce the weight and elastic memory of the plastic.

Figure 6A:
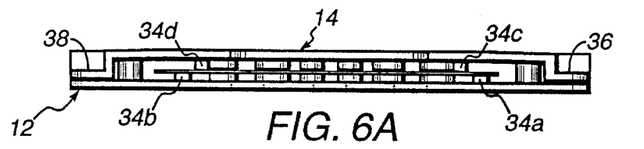
FIG. 6A is an enlarged end view similar to FIG. 6 with an object shown partially inserted into the folded insert member.

Referring to FIG. 6A, the test card 46 is shown as it would appear when passing the ramp-type stabilizing means 34a–34d. The stabilizing means 34a–34d gently grip and stabilize the card as it passes thereby into the object receiving pocket of the receptacle member 10. Additionally, movement of the test card past the stabilizing means operates to spread the first and second panels apart, thereby reducing the possibility that the bodily fluid samples may be contacted by internal receptacle structure during card insertion.

FIGS. 7 and 7A exemplify the manner in which a test card 46 may typically be inserted into the receptacle member 10. As illustrated, a corner of the leading edge of the card may initially come into contact with angled guide member 24 of the first guidance means. Upon exertion of insertion force at the trailing edge of the card, the card would slide along the guide member 24 until it would clear the guide member 24 and be substantially symmetrically positioned with respect to the insertion axis 22 of the receptacle member. At this stage, additional insertion force upon the card would cause the card to pass the guide members 30, 32 of the second guidance means which function to maintain the card's alignment during insertion. If present, the additional angled guide members 24a, 26a of the first guidance means and the additional guide members 30a, 32a of the second guidance means would function to correct any misalignment at the leading edge of the card as it comes to rest in the object receiving pocket of the receptacle member as shown in FIGS. 8 and 8A.

Referring again to FIG. 6 and also to FIGS. 8, 8A and 8B, it is preferable that the height of the stabilizing means' ramp members 34a, 34b outwardly project from the surface of first panel 12 to a height sufficient to overlap, in an elevational sense, their downwardly projecting counterparts 34c, 34d of second panel 14. Because of this preferred construction and also because of the elastic memory of the receptacle material, the stabilizing means captures the test card within the receptacle member once the card has passed the stabilizing means. Hence, the substantially vertical "rear" surfaces opposite the ramp surfaces of the stabilizing means ramp members 34a–34d, identified by reference numeral 68 in FIGS. 8 and 8A, establish means for retaining the test card within the receptacle's object receiving pocket. Such pocket may thus be envisioned as comprising the first and second guidance means, the hinge means 16 and the rear surfaces 68 of the stabilizing means' ramp members. In the event the envelope (described herebelow) within which the receptacle member 10 is received should inadvertently become opened during transport, retaining means 68 effectively prohibits a test card 46 or other object from escaping the object receiving pocket.

FIG. 9 reveals the geometry and other features of a presently preferred embodiment of an envelope 70 of the protective packaging system of the instant invention. FIG. 9 shows the interior surfaces of the envelope which cooperate to enclose the receptacle member 10 and thereby create a flexible yet rugged shipping package. Envelope 70 may be fabricated from any suitable flexible yet rugged material and, preferably, is made of paper or plastic, e.g., spun polyolefin such as Tyvek®. When paper is used, a suitable material may be solid, bleached sulfite stock ("SBS" stock). The envelope includes a central portion 72, an end flap 74, opposed side flaps 76 and 78, and a closure flap 80. The interior surfaces of the side flaps are desirably coated with a pressure-sensitive adhesive, although other adhesives would be equally acceptable. At least one or, more preferably, a plurality of heat-seal adhesive strips 82 or other adhesive (shown bounded by dashed lines) are preferably provided to insure secure bonding of the receptacle member 10 to envelope 70. In accordance with a presently preferred embodiment, one such strip 82 desirably spans the width of the central portion 72 adjacent closure flap 80 and another spans the width of the end flap 74 thereby assuring that both the first and second panels 12, 14 of the receptacle member become affixed to the envelope under application of sufficient heat, as described hereinafter. Lastly, the interior surface of the closure flap 80 bears an appropriate adhesive such as pressure-sensitive adhesive coated with release paper over a portion or, more preferably, the entirety thereof.

Figure 2:
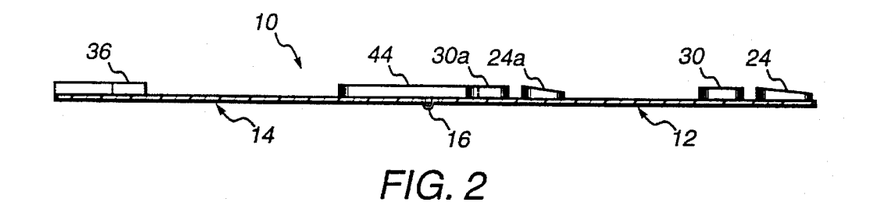
FIG. 2 is an elevational cross-section view of the receptacle member of FIG. 1 taken along line II—II thereof.
Figure 10:
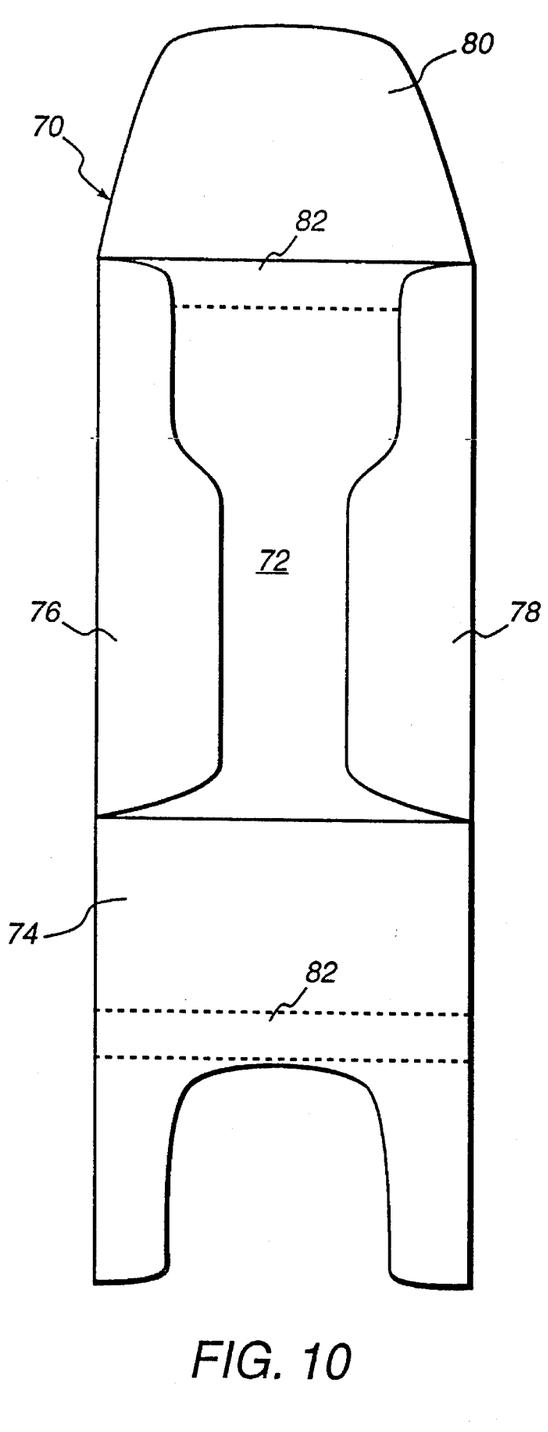
FIG. 10 is a top plan view depicting a first phase of assembly of the receptacle member and envelope of the protective packaging system of the present invention.
Figure 11:
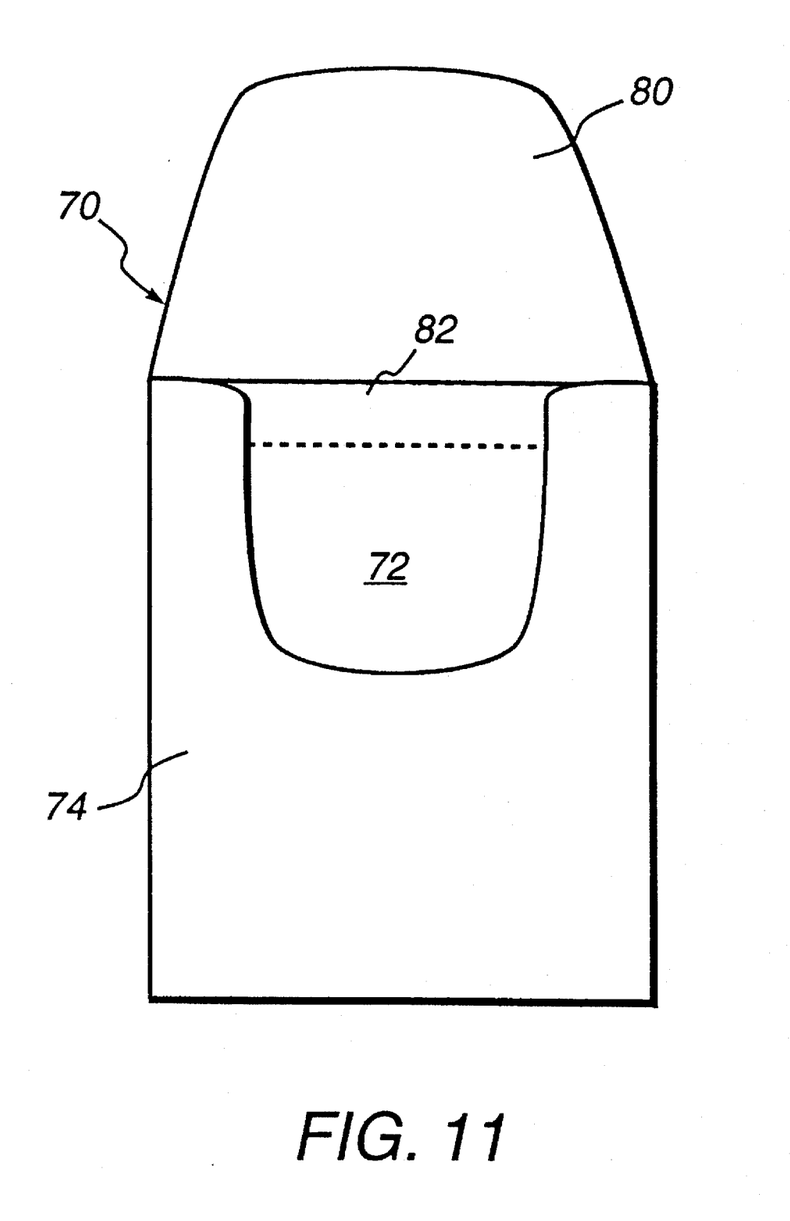
FIG. 11 is a top plan view depicting a further phase of assembly of the receptacle member and envelope of the protective packaging system of the present invention.
Figure 12:
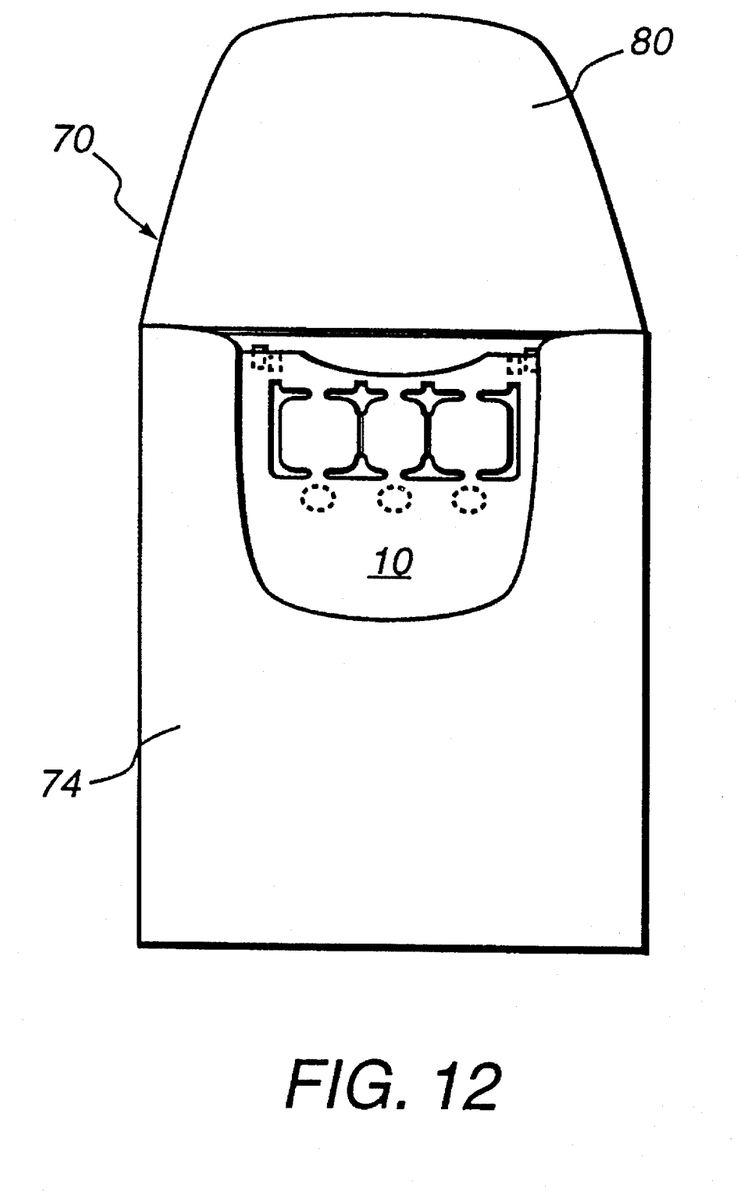
FIG. 12 is a top plan view depicting a further phase of assembly of the receptacle member and envelope of the protective packaging system of the present invention.

An exemplary although not exclusive method of assembling the receptacle member 10 and the envelope 70 is as follows. Initially, one folds the first and second panels 12, 14 of the receptacle member 10 and affixes same to one another to cause the receptacle to assume the folded configuration shown in FIG. 2. Referring to FIGS. 10 through 12, the side flaps 76, 78 of envelope 70 are then folded over onto the envelope central portion 72 (FIG. 10), followed thereafter by the end flap 74 (FIG. 11). The receptacle member 10 is then inserted, legs 40, 42 first, into the envelope (FIG. 12). For best results, it is preferable that the size and shape of the central envelope portion 72 be approximately the same as the base area of the first panel 12 of the receptacle member 10, as extended by legs 40, 42. Thus, by virtue of the legs, the receptacle fills out essentially the entire interior envelope area and is thereby effectively prevented from moving about inside the envelope during shipping. This is especially important when Tyvek® is used as the envelope material. Legs 40, 42 also act as a positioning device during insertion of the receptacle member into the envelope and, as previously mentioned, the legs impart to the mailer package a favorable balance of rigidity and flexibility, particularly when the legs include reinforcement ribs 44.

Once the receptacle member is properly received within the envelope the envelope side flaps 76, 78 may be RF sealed to bond the first and second panels 12, 14 to one another at protruding notches 36, 38. Lastly, the front surface of the envelope (i.e., the unillustrated exterior surface of central portion 72) may be passed over a heat source to melt the hot-melt adhesive strip(s) 82, hence providing, as previously mentioned, a presently preferred mechanism by which to secure the receptacle member to the envelope. In such condition, the combination of receptacle member 10 and envelope 70 may then function as a substantially flat protective packaging system capable of safely and rapidly transporting delicate flexible objects via the United States Postal Service or other carrier.

Figure 13:
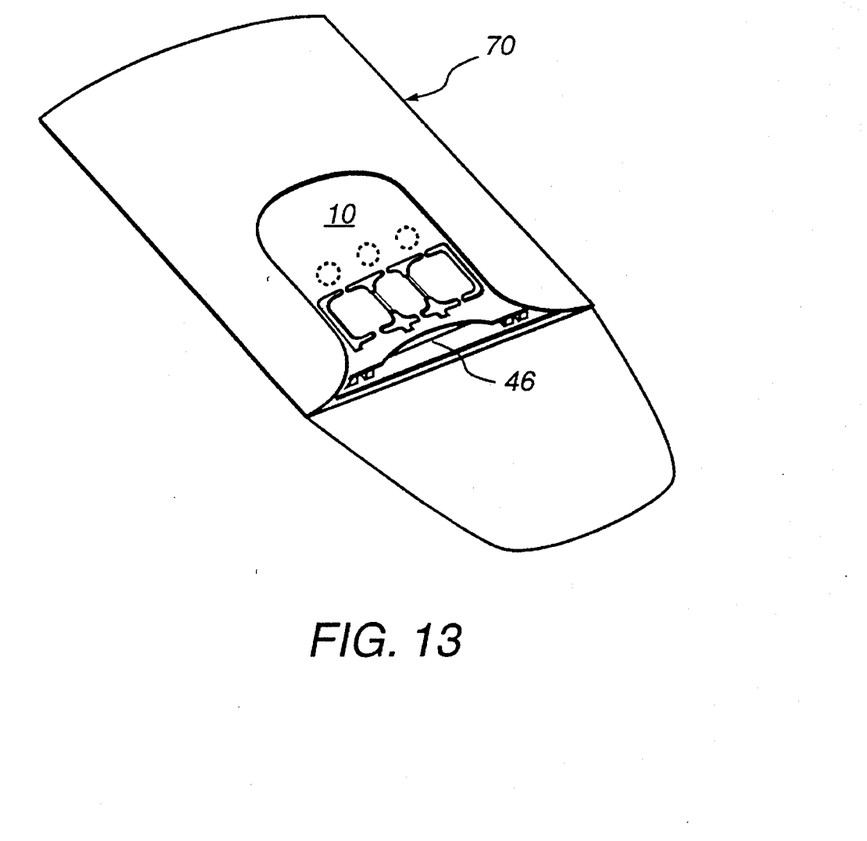
FIG. 13 is a perspective view of the protective packaging system of the present invention with an object fully inserted therein.

FIG. 13 shows the assembled mailer package with the test card fully inserted therein and the envelope closure flap 80 in open condition.

Figure 14:
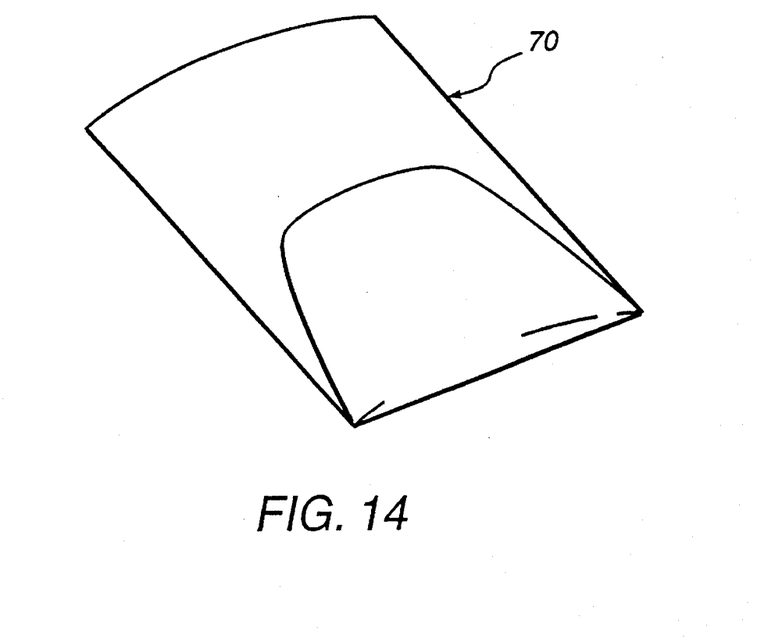
FIG. 14 is a perspective view of the protective packaging system of the present invention in condition for mailing.

As seen in FIG. 14, once the test card 46 or other object is fully inserted in the receptacle member as earlier described, the closure flap 80 is folded over and adhered to the end flap 74 whereby the protective package is ready for shipping. If the package's cargo is a medical specimen test card, the package is typically mailed to a test lab or similar facility. At the lab, the package may be opened by cutting or grinding with a grinding wheel along any edge of the package, but preferably along a longitudinal side edge thereof, so as to minimize the possibility of damage to the test card or its samples. The card may then be removed from the package by applying slight compressive force to the uncut package edges on either end of the cut to open the cut, and then gently shaking the package to free the card therefrom. In this way, human contact with the test card 46, and any potential transmission of infection associated with such contact, is effectively avoided.

The protective package is preferably designed such that when it is fully sealed, it is of dimensions suitable to permit its processing in automated postal service machinery rather than by more dilatory and inefficient hand processing. Moreover, the multiple ways (including adhesive strip 82) in which the receptacle member is preferably adhered to the envelope increase the likelihood that even a damaged envelope and its contents will eventually reach their intended destination. Adhesive strip 82 also prevents a test card or similar object from being improperly inserted between the first receptacle panel 12 and the interior surface of the central portion 72 of the envelope 70. Also, due to the seal between envelope end flap 74 and the first receptacle panel 14, the test card 46 or similar object cannot, without great difficulty, be inadvertently inserted therebetween. Accordingly, it is virtually impossible to improperly insert a medical specimen test card or other fragile object(s) into the mailer package.

Furthermore, as discussed, it is presently preferred that the receptacle member 10 be constructed and arranged such that an object is inserted into an end of the receptacle member along an insertion axis extending substantially parallel to the side edges of the receptacle member. It is also contemplated that the aforementioned guidance means and stabilizing means may be disposed in a direction substantially perpendicular to that shown in the drawing figures, whereby an object may be inserted laterally into the side of the receptacle member along an insertion axis extending substantially parallel to the end edges thereof.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A receptacle member adapted to receive an object, said receptacle member comprising:

a first panel;

a second panel;

means for securing said first and second panels in spaced apart, substantially facing relation to establish an insertion axis and an object receiving pocket between said first and second panels; and means carried by at least one of said first and second panels for facilitating insertion of an object into said object receiving pocket;

said means for facilitating insertion comprising means for displacing an object into a position substantially parallel to said insertion axis during insertion of an object into said object receiving pocket; and wherein said means for displacing comprise at least one pair of opposed guide members carried by at least one of said first and second panels, said guide members being angled inwardly toward said insertion axis in a direction of insertion of an object into said object receiving pocket.

2. The receptacle member of claim 1 wherein said receptacle member is fabricated from flexible material.

3. The receptacle member of claim 2 wherein said flexible material is plastic.

4. The receptacle member of claim 1 further comprising at least one aperture provided in at least one of said first and second panels for ventilating said object receiving pocket.

5. The receptacle member of claim 1 further comprising hinge means for foldably connecting said first and second panels.

6. A receptacle member adapted to receive an object, said receptacle member comprising:

a first panel;

a second panel;

means for securing said first and second panels in spaced apart, substantially facing relation to establish an insertion axis and an object receiving pocket between said first and second panels; and means carried by at least one of said first and second panels for facilitating insertion of an object into said object receiving pocket;

wherein said means for facilitating insertion comprise stabilizing means for urging an object to enter said object receiving pocket along a plane extending substantially parallel to at least one of said first and second panels during insertion of an object into said object receiving pocket.

7. The receptacle member of claim 6 wherein said stabilizing means comprise at least one ramp member projecting from at least one of said first and second panels.

8. The receptacle member of claim 7 wherein said stabilizing means comprise a ramp member carried by each of said first and second panels.

9. The receptacle member of claim 8 wherein said stabilizing means comprise a pair of ramp members carried by at least one of said first and second panels.

10. The receptacle member of claim 9 wherein said stabilizing means comprise a pair of ramp members carried by each of said first and second panels.

11. The receptacle member of claim 7 wherein said stabilizing means further comprise means for retaining an object within said object receiving pocket when an object is fully received within said object receiving pocket.

12. The receptacle member of claim 11 wherein said means for retaining comprise at least one surface opposite a ramp surface of said at least one ramp member.

13. The receptacle member of claim 6 further comprising means carried by at least one of said first and second panels for retaining an object within said object receiving pocket when an object is fully received within said object receiving pocket.

14. The receptacle member of claim 6 further comprising structure carried by at least one of said first and second panels for covering and protecting at least one predetermined area of an object to be inserted into said object receiving pocket.

15. The receptacle member of claim 14 wherein said structure is located along at least one edge region of said first and second panels.

16. The receptacle member of claim 15 wherein said structure is located along opposite edge regions of said first and second panels.

17. The receptacle member of claim 14 wherein said structure is carried by each of said first and second panels.

18. The receptacle member of claim 14 wherein said structure is located at at least one of an upstream region and a downstream region of said first and second panels relative to a direction of insertion of an object into said object receiving pocket.

19. The receptacle member of claim 18 wherein said structure is located at each of an upstream region and a downstream region of said first and second panels relative to a direction of insertion of an object into said object receiving pocket.

20. The receptacle member of claim 14 wherein said structure comprises at least one substantially dome-shaped structure including:

at least one wall projecting from at least one of said first and second panels; and at least one surface of at least one of said first and second panels bounded by said at least one wall.

21. The receptacle member of claim 20 wherein said at least one wall is continuous.

22. The receptacle member of claim 20 wherein said at least one wall is provided with at least one gap.

23. The receptacle member of claim 22 wherein said at least one gap is situated substantially along a longitudinal axis of said structure, said longitudinal axis extending substantially parallel to said insertion axis.

24. The receptacle member of claim 22 wherein said at least one gap is situated substantially along a transverse axis of said structure, said transverse axis extending substantially transverse to said insertion axis.

25. The receptacle member of claim 14 which said means for facilitating insertion further comprise means carried by at least one of said first and second panels for facilitating movement of an object past said structure during insertion of an object into said object receiving pocket.

26. The receptacle member of claim 25 wherein said means for facilitating movement comprise at least one ramp member projecting from at least one of said first and second panels upstream of said structure relative to a direction of insertion of an object into said object receiving pocket.

27. The receptacle member of claim 26 wherein said at least one ramp member is integral with said structure.

28. A receptacle member adapted to receive an object, said receptacle member comprising:

a first panel;

a second panel;

means for securing said first and second panels in spaced apart, substantially facing relation to establish an insertion axis and an object receiving pocket between said first and second panels;

means carried by at least one of said first and second panels for displacing an object into a position substantially parallel to said insertion axis during insertion of an object into said object receiving pocket; and stabilizing means for urging an object to enter said object receiving pocket along a plane extending substantially parallel to at least one of said first and panels second during insertion of an object into said object receiving pocket.

29. The receptacle member of claim 28 wherein said means for displacing comprise at least one pair of opposed angled guide members carried by at least one of said first and second panels, said angled guide members being angled inwardly toward said insertion axis in a direction of insertion of an object into said object receiving pocket.

30. The receptacle member of claim 28 further comprising means for maintaining an object in substantially parallel orientation to said insertion axis during insertion of an object into said object receiving pocket.

31. The receptacle member of claim 30 wherein said means for maintaining comprise at least one pair of opposed guide members carried by at least one of said first and second panels, said guide members extending substantially parallel to said insertion axis.

32. The receptacle member of claim 30 wherein said means for maintaining are located downstream of said means for displacing relative to a direction of insertion of an object into said object receiving pocket.

33. The receptacle member of claim 28 wherein said stabilizing means comprise at least one ramp member projecting from at least one of said first and second panels.

34. The receptacle member of claim 33 wherein said stabilizing means comprise a ramp member carried by each of said first and second panels.

35. The receptacle member of claim 34 wherein said stabilizing means comprise a pair of ramp members carried by at least one of said first and second panels.

36. The receptacle member of claim 35 wherein said stabilizing means comprise a pair of ramp members carried by each of said first and second panels.

37. The receptacle member of claim 33 wherein said stabilizing means further comprise means for retaining an object within said object receiving pocket when an object is fully received within said object receiving pocket.

38. The receptacle member of claim 37 wherein said means for retaining comprise at least one surface opposite a ramp surface of said at least one ramp member.

39. The receptacle member of claim 28 further comprising means carried by at least one of said first and second panels for retaining an object within said object receiving pocket when an object is fully received within said object receiving pocket.

40. The receptacle member of claim 28 further comprising structure carried by at least one of said first and second panels for covering and protecting at least one predetermined area of an object to be inserted into said object receiving pocket.

41. The receptacle member of claim 40 wherein said structure is located along at least one edge region of said first and second panels.

42. The receptacle member of claim 41 wherein said structure is located along opposite edge regions of said first and second panels.

43. The receptacle member of claim 40 wherein said structure is carried by each of said first and second panels.

44. The receptacle member of claim 40 wherein said structure is located at at least one of an upstream region and a downstream region of said first and second panels relative to a direction of insertion of an object into said object receiving pocket.

45. The receptacle member of claim 44 wherein said structure is located at each of an upstream region and a downstream region of said first and second panels relative to a direction of insertion of an object into said object receiving pocket.

46. The receptacle member of claim 40 wherein said structure comprises at least one substantially dome-shaped structure including:
   at least one wall projecting from at least one of said first and second panels; and
   at least one surface of at least one of said first and second panels bounded by said at least one wall.

47. The receptacle member of claim 46 wherein said at least one wall is continuous.

48. The receptacle member of claim 46 wherein said at least one wall is provided with at least one gap.

49. The receptacle member of claim 48 wherein said at least one gap is situated substantially along a longitudinal axis of said structure, said longitudinal axis extending substantially parallel to said insertion axis.

50. The receptacle member of claim 48 wherein said at least one gap is situated substantially along a transverse axis of said structure, said transverse axis extending substantially transverse to said insertion axis.

51. The receptacle member of claim 40 which said means for facilitating insertion further comprise means carried by at least one of said first and second panels for facilitating movement of an object past said structure during insertion of an object into said object receiving pocket.

52. The receptacle member of claim 51 wherein said means for facilitating movement comprise at least one ramp member projecting from at least one of said first and second panels upstream of said structure relative to a direction of insertion of an object into said object receiving pocket.

53. The receptacle member of claim 52 wherein said at least one ramp member is integral with said structure.

54. A receptacle member adapted to receive an object, said receptacle member comprising:
   a first panel;
   a second panel;
   means for securing said first and second panels in spaced apart, substantially facing relation to establish an insertion axis and an object receiving pocket between said first and second panels; and
   structure carried by at least one of said first and second panels for covering and protecting at least one predetermined area of an object to be inserted into said object receiving pocket;
   wherein said structure comprises at least one substantially dome-shaped structure including;
   at least one wall projecting from at least one of said first and second panels;
   at least one surface of at least one of said first and second panels bounded by said at least one wall; and
   wherein said at least one wall is provided with at least one gap.

55. The receptacle member of claim 54 wherein said structure is located along at least one edge region of said first and second panels.

56. The receptacle member of claim 55 wherein said structure is located along opposite edge regions of said first and second panels.

57. The receptacle member of claim 54 wherein said structure is carried by each of said first and second panels.

58. The receptacle member of claim 54 wherein said structure is located at at least one of an upstream region and a downstream region of said first and second panels relative to a direction of insertion of an object into said object receiving pocket.

59. The receptacle member of claim 58 wherein said structure is located at each of an upstream region and downstream region of said first and second panels relative to a direction of insertion of an object into said object receiving pocket.

60. The receptacle member of claim 54 wherein said at least one wall is continuous.

61. The receptacle member of claim 54 wherein said at least one gap is situated substantially along a longitudinal axis of said structure, said longitudinal axis extending substantially parallel to said insertion axis.

62. The receptacle member of claim 54 wherein said at least one gap is situated substantially along a transverse axis of said structure, said transverse axis extending substantially transverse to said insertion axis.

63. The receptacle member of claim 54 which said means for facilitating insertion further comprise means carried by at least one of said first and second panels for facilitating movement of an object past said structure during insertion of an object into said object receiving pocket.

64. The receptacle member of claim 63 wherein said means for facilitating movement comprise at least one ramp member projecting from at least one of said first and second panels upstream of said structure relative to a direction of insertion of an object into said object receiving pocket.

65. The receptacle member of claim 64 wherein said at least one ramp member is integral with said structure.

66. A protective packaging system comprising:
   (a) a receptacle member including:
      a first panel;
      a second panel;
      means for securing said first and second panels in spaced apart, substantially facing relation to establish an insertion axis and an object receiving pocket between said first and second panels; and
      means carried by at least one of said first and second panels for facilitating insertion of an object into said object receiving pocket; and
      said means for facilitating insertion comprise means for displacing an object into a position substantially parallel to said insertion axis during insertion of an object into said object receiving pocket; and
      wherein said means for displacing comprise at least one pair of opposed guide members carried by at least one of said first and second panels, said guide members being angled inwardly toward said insertion axis in a direction of insertion of an object into said object receiving pocket; and
   (b) an envelope adapted for enclosing said receptacle member.

67. A protective packaging system comprising:
   (a) a receptacle member including:
      a first panel;
      a second panel;
      means for securing said first and second panels in spaced apart, substantially facing relation to establish an insertion axis and an object receiving pocket between said first and second panels; and means carried by at least one of said first and second panels for displacing an object into a position substantially parallel to said insertion axis during insertion of an object into said object receiving pocket;

stabilizing means for urging an object to enter said object receiving pocket along a plane extending substantially parallel to at least one of said first and panels second during insertion of an object into said object receiving pocket; and further comprising at least one substantially dome-shaped structure including:

at least one wall projecting from at least one of said first and second panels; and at least one surface of at least one of said first and second panels bounded by said at least one wall;

(b) an envelope adapted for enclosing said receptacle member.

68. A protective packaging system comprising:

(a) a receptacle member including:

a first panel;

a second panel;

means for securing said first and second panels in spaced apart, substantially facing relation to establish an insertion axis and an object receiving pocket between said first and second panels; and structure carried by at least one of said first and second panels for covering and protecting at least one predetermined area of an object to be inserted into said object receiving pocket; and (b) an envelope adapted for enclosing said receptacle member.

69. The protective packaging system of claim 67 wherein said envelope is fabricated from paper.

70. The protective packaging system of claim 67 wherein said envelope is fabricated from plastic.

71. The protective packaging system of claim 67 wherein said receptacle member is fabricated from flexible material.

72. The protective packaging system of claim 67 wherein said flexible material is plastic.

73. The protective packaging system of claim 67 wherein said receptacle member further comprises means for imparting substantial rigidity to said protective packaging system.

74. The protective packaging system of claim 73 wherein said means for imparting substantial rigidity comprise leg members projecting from one of said first and second panels.

75. The protective packaging system of claim 74 wherein each of said leg members includes at least one elongated rib.

76. The protective packaging system of claim 67 further comprising means for preventing movement of said receptacle member within said envelope.

77. The protective packaging system of claim 76 wherein said means for preventing movement comprise means for adhesively connecting said receptacle member to an interior surface of said envelope.

78. The protective packaging system of claim 76 wherein said means for preventing movement comprise leg members projecting from one of said first and second panels.

79. A receptacle member adapted to receive an object, said receptacle member comprising:

a first panel;

a second panel;

means for securing said first and second panels in spaced apart, substantially facing relation to establish an insertion axis and an object receiving pocket between said first and second panels; and means carried by at least one of said first and second panels for facilitating insertion of an object into said object receiving pocket;

wherein said means for facilitating insertion comprise means for maintaining an object in substantially parallel orientation to said insertion axis during insertion of an object into said object receiving pocket; and wherein said means for maintaining comprise at least one pair of opposed guide members carried by at least one of said first and second panels, said guide members extending substantially parallel to said insertion axis.

* * * * *